United States Patent
Commereuc et al.

(10) Patent No.: US 6,686,510 B2
(45) Date of Patent: Feb. 3, 2004

(54) PRODUCTION OF HIGH-PURITY ISOBUTENE AND PROPYLENE FROM HYDROCARBON FRACTIONS WITH FOUR CARBON ATOMS

(75) Inventors: Dominique Commereuc, Meudon (FR); Blaise Didillon, Francheville (FR); Helene Olivier-Bourbigou, Rueil Malmaison (FR); Lucien Saussine, Croissy sur Seine (FR)

(73) Assignee: Institut Français du Petrole, Reuil-Malmaison (FR)

( * ) Notice: Subject to any disclaimer, the term of this patent is extended or adjusted under 35 U.S.C. 154(b) by 143 days.

(21) Appl. No.: 09/745,722

(22) Filed: Dec. 26, 2000

(65) Prior Publication Data

US 2002/0169346 A1 Nov. 14, 2002

(30) Foreign Application Priority Data

Dec. 24, 1999 (FR) .............................. 99 16507

(51) Int. Cl.$^7$ .............................. C07C 5/22; C07C 6/04
(52) U.S. Cl. .................. 585/324; 585/671; 585/332; 585/644; 585/646; 585/647; 585/259; 585/262
(58) Field of Search ................................ 585/324, 332, 585/259, 262, 644, 646, 647, 671

(56) References Cited

U.S. PATENT DOCUMENTS

| | | | | |
|---|---|---|---|---|
| 5,227,553 A | * | 7/1993 | Polanek et al. | ............. 585/259 |
| 5,281,753 A | * | 1/1994 | Olson et al. | ................. 585/259 |
| 5,523,502 A | * | 6/1996 | Rubin | ......................... 568/697 |
| 5,877,363 A | * | 3/1999 | Gildert et al. | ................. 203/29 |
| 6,075,173 A | * | 6/2000 | Chodorge et al. | ............. 208/49 |
| 6,137,023 A | * | 10/2000 | Dorbon et al. | ................. 203/28 |
| 6,166,279 A | * | 12/2000 | Schwab et al. | ............. 585/312 |
| 6,169,218 B1 | * | 1/2001 | Hearn et al. | ........... 203/DIG. 6 |
| 6,207,115 B1 | * | 3/2001 | Chodorge et al. | ........... 422/131 |
| 6,242,661 B1 | * | 6/2001 | Podrebarac et al. | .......... 203/29 |

FOREIGN PATENT DOCUMENTS

FR  2 755 130  4/1998

* cited by examiner

*Primary Examiner*—Walter D. Griffin
(74) *Attorney, Agent, or Firm*—Millen, White, Zelano & Branigan, P.C.

(57) ABSTRACT

A process for production, from an olefinic $C_4$ fraction, on the one hand, of high-purity isobutene and, on the other hand, of propylene by metathesis is described. The process comprises three successive stages:

Figure 1:
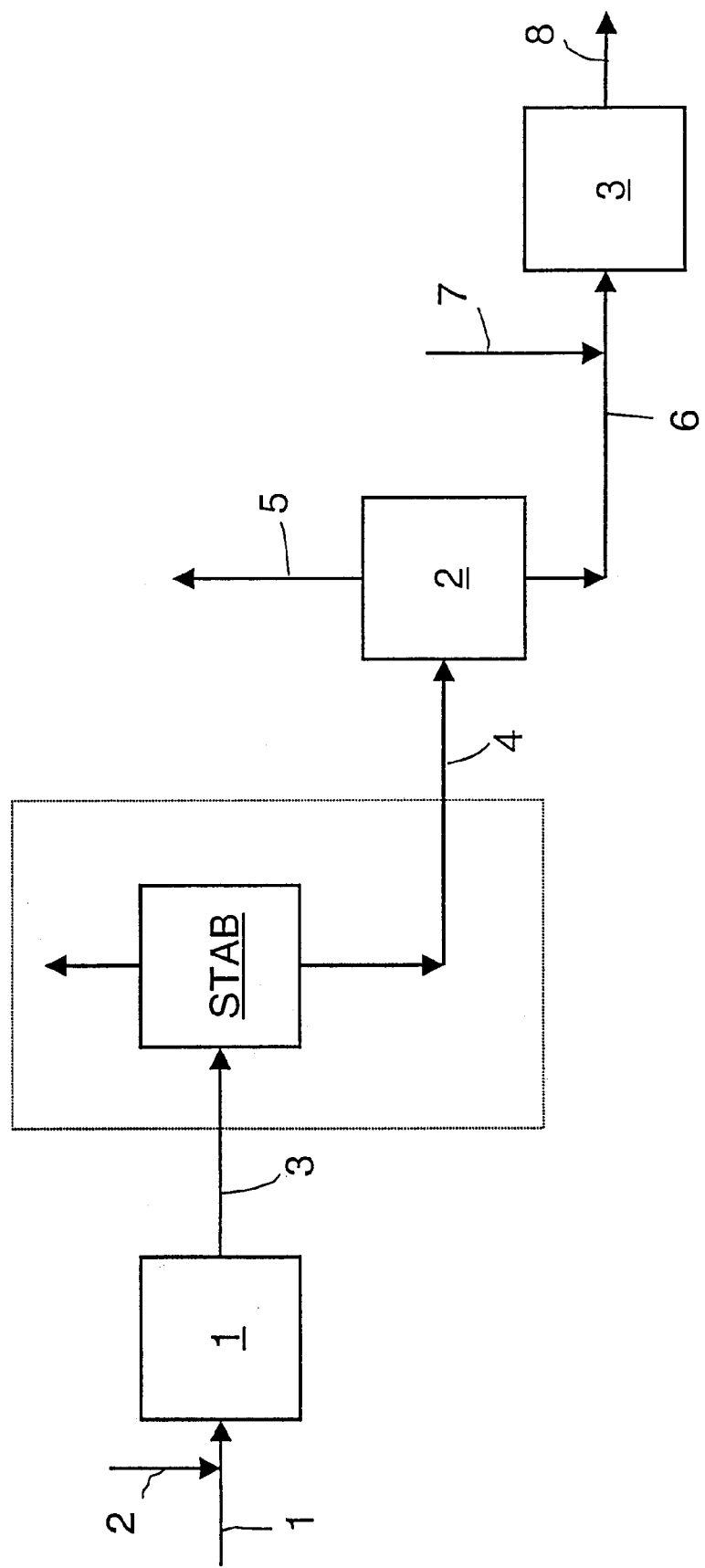

1) the selective hydrogenation of butadiene with isomerization of butene-1 into butene-2 up to thermodynamic equilibrium;
2) the separation by isobutene at the column head that integrates the hydroisomerization of n-butenes, allowing a butene-2 fraction at the bottom, and
3) the metathesis of the butene-2 fraction with ethylene.

By this process, it is possible to produce in a very selective way high-purity isobutene and polymerization-quality propylene.

20 Claims, 1 Drawing Sheet

PRODUCTION OF HIGH-PURITY ISOBUTENE AND PROPYLENE FROM HYDROCARBON FRACTIONS WITH FOUR CARBON ATOMS

CROSS-REFERENCE TO RELATED APPLICATION

This application is related to Applicants concurrently filed application Ser. No. 09/745,728, entitled "Process For Selective Production Of Propylene From Hydrocarbon Fractions With Four Carbon Atoms", now abandoned, based on French Application 99/16.506 filed Dec. 24, 1999.

The invention relates to a process for production of high-purity isobutene and propylene from a $C_4$ fraction.

The steam-cracking of feedstocks that consist of light paraffinic fractions produces the ethylene and the propylene that are necessary to petrochemistry. It also produces a certain number of other heavier products, and in particular a $C_4$ hydrocarbon fraction that contains mainly butadiene-1,3, isobutene, n-butenes and butanes, accompanied by traces of acetylenic hydrocarbons.

The catalytic cracking of heavy hydrocarbon feedstocks produces, alongside gasoline and gasoil fractions that are the main products, lighter products, including a $C_4$ hydrocarbon fraction that contains mainly isobutane, isobutene, n-butenes and butanes, accompanied by small amounts of butadiene-1,3 and acetylenic hydrocarbons.

Until recently, only butadiene-1,3 and isobutene were used in the polymer industry, in particular in the tire industry. The increase of the longevity of tires and a relative stagnation of the demand ensure that there is now excess butadiene that is not used or is poorly used. On the contrary, interest was rekindled for isobutene, which can be used as, for example, a monomer in the synthesis of polyisobutene.

This invention proposes a process for treatment of a $C_4$ hydrocarbon fraction that contains primarily isobutene, n-butenes, butanes, and butadiene-1,3 in a variable amount that includes the separation of isobutene by means of a catalytic distillation in which the butene-1 that is impossible to separate from the isobutene is isomerized in butenes-2, and that makes it possible to transform the butadiene-1,3 and the n-butenes into propylene that can be used for, for example, polymerization.

The relative proportions of ethylene and propylene that are produced in a steam-cracking operation can be modulated to a certain extent by changing the nature of the feedstock and by modifying the operating conditions (the degree of rigor) of the cracking. The operating method that is oriented toward a larger proportion of propylene, however, inevitably entails a decline in the yield of ethylene and a higher $C_4$ fraction and gasoline fraction production.

Another object of this invention is to increase the propylene production while maintaining a high ethylene yield with the treatment of the $C_4$ hydrocarbon fraction and therefore without it being necessary to reduce the rigorous conditions of the steam-cracking device.

The process that is the object of the invention is more specifically a process for converting an olefinic $C_4$ fraction into high-purity isobutene and into propylene, whereby said fraction contains in particular diolefins, butene-1, butenes-2, isobutene and acetylenic impurities, and whereby said process comprises the following stages that take place successively:

1) the selective hydrogenation of diolefins and acetylenic impurities with isomerization of butene-1 into butenes-2 in the presence of a catalyst, in order to obtain an effluent that contains n-butenes, whose ratio corresponds to the thermodynamic equilibrium and isobutene, and that contains virtually no diolefins or acetylenic compounds;

2) the separation, by distillation, of a top fraction that contains isobutene and a bottom fraction that contains essentially butenes-2 and butane; and 3) the metathesis of the butenes-2 fraction that is obtained from the preceding stage with the ethylene, in the presence of a catalyst, so as to obtain an effluent that contains propylene, whereby the metathesis is followed by a separation of the propylene;

whereby said process is characterized in that stage 2 is implemented in a column that integrates the hydroisomerization of butene-1 that remains in butenes-2, and in that the top fraction contains essentially the starting isobutene that is free of butene-1.

The special conditions of the different stages of the process according to the invention, carried out from a $C_4$ hydrocarbon fraction that contains primarily isobutene, n-butenes, butanes, as well as butadiene in a variable amount, whereby said $C_4$ fraction is subjected to these stages to produce isobutene and propylene, will be described in more detail below.

The main object of the first stage is to transform the butadiene and the butene-1 into butenes-2. Actually, the butenes-2 are the source of the propylene that is produced in the last stage of metathesis in the presence of ethylene. It is therefore desirable to increase as much as possible the butenes-2 yield, i.e., to draw as close as possible to the ratio that is allowed by thermodynamics. The second object of this stage is to eliminate the acetylenic hydrocarbon traces that are always present in these fractions and that are poisons or contaminants for the subsequent stages.

In this first stage, the following reactions are therefore carried out simultaneously in the presence of hydrogen:

the selective hydrogenation of butadiene into a mixture of n-butenes at thermodynamic equilibrium;

the isomerization of butene-1 into butenes-2 to obtain a distribution that is close to the thermodynamic equilibrium of the n-butenes, and the selective hydrogenation of the acetylenic hydrocarbon traces into butenes.

These reactions can be carried out with various specific catalysts that comprise one or more metals, for example from group 10 of the periodic table (Ni, Pd or Pt), deposited on a substrate. A catalyst that comprises at least one palladium compound that is fixed on a refractory mineral substrate, for example on an alumina, is preferably used. The palladium content in the substrate can be 0.01 to 5% by weight, preferably 0.05 to 1% by weight. Various pretreatment methods that are known to one skilled in the art optionally can be applied to these catalysts to improve the selectivity in the hydrogenation of butadiene into butenes at the expense of the total hydrogenation of butane that it is necessary to avoid, and to promote the hydroisomerization of the n-butenes (from butene-1 into butenes-2). The catalyst preferably contains 0.05 to 10% by weight of sulfur. Advantageously, a catalyst is used that consists of palladium that is deposited on alumina, and sulfur.

The catalyst can advantageously be used according to the process that is described in Patent FR-B-2 708 596, i.e., the catalyst was treated, before being loaded into the hydrogenation reactor, by at least one sulfur-containing compound that is diluted in a solvent, then the catalyst that is obtained that contains 0.05 to 10% by weight of sulfur is loaded into the reactor and activated under a neutral atmosphere or a reducing atmosphere at a temperature of 20 to 300° C., a pressure of 0.1 to 5 MPa and a VVH of 50 to 600 h$^{-1}$, and the feedstock is brought into contact with said activated catalyst.

The use of the catalyst, preferably with palladium, is not critical, but it is generally preferred to use at least one down-flow reactor through a catalyst fixed bed. When the proportion of butadiene in the fraction is large, which is the case, for example, of a steam-cracking fraction when it is not desired to extract the butadiene from it for specific uses, it may be advantageous to carry out the transformation in two reactors in series to better monitor the selectivity of the hydrogenation. The second reactor can have a rising flow and play a finishing role.

The amount of hydrogen that is necessary for all of the reactions that are carried out in this stage is adjusted based on the composition of the fraction advantageously to have only a slight hydrogen excess relative to the stoichiometry.

The operating conditions are selected such that the reagents and the products are in liquid phase. It may be advantageous, however, to select an operating mode such that the products are partially evaporated at the outlet of the reactor, which facilitates the thermal monitoring of the reaction. The temperature may vary from 20 to 200° C., preferably from 50 to 150° C. or better from 60 to 100° C. The pressure may be adjusted to a value of 0.1 to 5 MPa, preferably 0.5 to 4 MPa, and advantageously from 0.5 to 3 MPa, such that the reagents, at least in part, are in liquid phase. The volumetric flow rate may be from 0.5 to 20 h$^{-1}$ and preferably from 1 to 10 h$^{-1}$, with an H$_2$/diolefin molar ratio of 0.5 to 5 and preferably 1 to 3.

The reactor or reactors that are used to implement stage 1 of selective hydrogenation and isomerization may advantageously be followed by a stabilization column that eliminates the traces of gaseous hydrocarbons that are optionally present in the feedstock hydrogen.

The object of the second stage is to separate, in a column that integrates the hydroisomerization of the n-butenes (i.e., the butene-1 that remains after stage 1 in butenes-2), the C$_4$ fraction that is obtained from stage 1 to obtain, on the one hand, at the top a fraction that contains essentially isobutene, and, on the other hand, at the bottom a fraction that contains a small amount of butene-1, butenes-2 and n-butane. The isobutene that is thus concentrated may be intended for various uses. The butenes-2 fraction is directed toward the metathesis stage.

The column that integrates the hydroisomerization of the n-butenes comprises, on the inside or outside, one or more feedstocks of a catalyst of the same type as the one that is used in stage 1. The column that integrates the hydroisomerization of the n-butenes that is used in the process according to the invention can be of any type. In a preferred arrangement, at least one zone that contains the catalyst is arranged. The mechanical arrangement of the catalyst in the catalytic zone or zones should be such that it disturbs the flows of vapor and liquid as little as possible between the two separation zones that frame it. The catalyst can be placed, for example, in a thin layer on perforated plates or on grids, or in bags that are suspended or laid on substrates that ensure their mechanical behavior, or any other way that is known to one skilled in the art. On the other hand, the catalyst can be placed in the column so that only an upward flow of liquid phase passes through it. It can also be arranged in the form of catalytic packing according to the different implementations that are known. The separation zones that frame the catalytic zones can comprise plates or packing. One of the uses of the column can correspond to, for example, Patent FR-B-2 755 130, in the name of the applicant.

The butenes-2 fraction that is obtained from stage 2 can be sent directly into the third stage of the process. In this last stage, the butenes-2 are reacted with ethylene to produce propylene by metathesis. Because of the small amount of butene-1 and isobutene in the feedstock, the by-product formation is very limited.

The metathesis reaction of the ethylene with the butenes-2 in stage 3 can be catalyzed by varied metallic oxides that are deposited on substrates. A catalyst that comprises at least one rhenium oxide that is deposited on a substrate that consists of a refractory oxide that contains at least alumina, which has an acidic nature, such as, for example, alumina itself, silica-aluminas or zeolites, is preferably used.

It is possible to cite, by way of preferred examples, the catalysts that comprise rhenium heptoxide that is deposited on a gamma-alumina, analogously to the one that is used in the reforming catalysts, as described in U.S. Pat. No. 4,795, 734. The rhenium content (expressed in metallic rhenium) can be 0.01 to 20%, preferably 1 to 15% by weight. The catalysts are subjected to, for example, a final thermal activation at a temperature of 400 to 1000° C. for a period of 10 minutes to 5 hours under a non-reducing atmosphere.

The catalysts that comprise rhenium heptoxide that is deposited on an alumina can also be modified by the addition of an oxide of another metal. Such modified catalysts comprise, for example, rhenium in the oxide state, from 0.01 to 20% by weight expressed in metallic rhenium, deposited on a substrate that contains at least 75% by weight of alumina and 0.01 to 30% by weight of at least one oxide of a metal that is selected from the group that is formed by niobium and tantalum, as described in Patent FR-B-2 709 125.

The metathesis reaction is carried out preferably in a liquid phase, without oxygen, oxidized compounds and moisture, and at a temperature of 0 to 200° C., preferably 20 to 150° C., under a pressure that is at least equal to the vapor pressure of the reaction mixture at the reaction temperature.

The catalyst can be used in a fixed bed. Since it must be regenerated frequently, however, it is generally necessary to use at least two reactors in parallel, whereby one is in use while the other is being regenerated. A catalyst moving bed system as it is described in French Patent FR-B-2 608 595 is preferably used. The catalyst is drawn off at regular intervals from the bottom of the reactor and transferred to a continuous regeneration system, from where it is sent to the top of the reactor.

Taking into account the limitations that are imposed by thermodynamics, the unconverted ethylene is fractionated in a first distillation column and recycled in the metathesis reactor. A second distillation column separates the propylene and the unconverted C$_4$ hydrocarbons that can be recycled in the metathesis reactor. The fractionation diagram is therefore simpler than if a large amount of butene-1 had been present in the feedstock, because it would then have formed more pentenes and hexenes that it would have been necessary to eliminate before recycling the butenes.

When the process is applied to a steam-cracking C$_4$ fraction, it may be advantageous to integrate the metathesis unit with the cracking device to take advantage of the fractionation train of the latter. The ethylene that is obtained from the steam-cracking operation is then used in the metathesis stage.

The succession of treatments adopted in the process according to the invention has many advantages. The most reactive compounds of the fraction, in particular the butadiene-1,3 that is present in variable amounts, as well as the traces of acetylenic hydrocarbons, are transformed from the first stage and therefore will not be the cause of parasitic reactions in the following stages. Furthermore, the selective hydrogenation of diolefins (butadiene-1,3 and butadiene-1,2) into butenes and the hydroisomerization of butene-1 coupled to the separation in a column that integrates the hydroisomerization of n-butenes make it possible to increase considerably the butenes-2 concentration in the fraction while reducing to low values the butene-1 concentration, which thereby promotes a high yield of propylene in the metathesis stage.

Actually, the butene-1 reacts by metathesis with the butenes-2 to produce propylene and pentenes, and it reacts with itself to produce hexenes. Pentenes and hexenes are by-products of low value, which it is necessary to eliminate, in a costly manner. The process therefore makes possible an appreciable increase of the propylene yield and facilitates the recycling of butenes-2 in the metathesis reactor, since there are few pentenes and hexenes to eliminate.

The invention also relates to an installation (illustrated by FIG. 1) that is used to implement the process that is described above.

It successively comprises:

- a zone 1 for selective hydrogenation with isomerization of butene-1 into butenes-2, whereby said zone comprises at least one means 1 for introducing the fraction that is to be converted, at least one means 3 for the output of the effluent and at least one means 2 for the introduction of hydrogen, whereby said zone also comprises at least one catalyst bed that preferably comprises at least one metal that is selected from the group that is formed by nickel, palladium and platinum, deposited on a substrate;
- a zone 2 for separation, in a column that integrates the hydroisomerization of the n-butenes (butene-1 remaining after stage 1 in butenes-2), that comprises at least one means 3 for the introduction of the effluent that is obtained from zone 1, at least one means 5 for the output of isobutene, at least one means 4 for the output of butenes-2 and n-butane; and
- a zone 3 for metathesis that contains at least one catalyst preferably with a rhenium oxide base that is deposited on a substrate and that comprises at least one means 6 for introducing the effluent that is obtained from zone 2, at least one means 7 for introducing ethylene and at least one means 8 for the output of the propylene.

In a particularly advantageous way, the $C_4$ fraction is obtained from an upstream steam-cracking zone, whereby the means for introducing the fraction that is to be converted into zone 1 is connected to said steam-cracking zone, and the means for introducing the ethylene into zone 4 is connected to said steam-cracking zone.

The following examples illustrate the invention without limiting its scope.

EXAMPLE 1

A $C_4$ fraction at the outlet of the steam-cracking device has the composition that is indicated in Table 1 (flow 1). In this table, the abbreviations have the following meanings:

MAPD=methylacetylene+propadiene,
BBV=butadiene-1,2+butyne-1+vinylacetylene.

The $C_4$ fraction that is to be treated is first subjected to a hydrogenation and hydroisomerization treatment. It is introduced continuously, with the mass flow rate indicated in Table 1, and under a pressure of 2 MPa, in a first reactor that comprises a fixed bed of 2.6 T of a catalyst that consists of palladium on alumina that was sulfurized in advance.

Hydrogen (mixed with methane) is also injected into this reactor, as indicated in Table 1 (flow 2). To limit the temperature increase in the catalytic bed, the feedstock is mixed with the effluent of the reactor in a ratio of 1 per 20 before treatment. The effluent of this first reactor is then treated in a finishing reactor that is loaded with 2.5 T of the same catalyst. At the outlet (Table 1, flow 3), acetylenic compounds are removed from the fraction, and the butadiene was transformed essentially into butenes, which are for the most part butenes-2, butene-1 having been isomerized. The fraction is then treated in a stabilization column, where the residual hydrogen and the methane are separated. After this treatment, the fraction has the composition of flow 4 (Table 1).

In the second stage, the hydroisomerized $C_4$ fraction is subjected to a fractionation in a column that integrates the hydroisomerization of the n-butenes (whereby butene-1 remains after stage 1 in butenes-2). This column comprises 130 plates, is fed at plate 90, and is equipped with three coupled reactors that are loaded with the same catalyst as the one that is used in the first stage and whose inlet and outlet are connected directly to the column, respectively at the level of plates 10–11, 25–26 and 39–40. The reflux rate and the temperatures are adjusted to obtain an almost pure isobutene flow at the top.

In the third stage, the bottom distillation fraction that contains primarily butene-2 is reacted with ethylene (overall composition: flows 6 and 7 of Table 1) on a metathesis catalyst that consists of rhenium oxide on gamma-alumina (8% by weight of metal rhenium), prepared according to the teachings of U.S. Pat. No. 4,795,734. The $C_4$ fraction is mixed at the inlet of the metathesis reactor with make-up ethylene, as well as with ethylene and butene recycling flows. This reactor operates in a moving bed, as described in Patent FR-B-2 608 595, at a temperature of 35° C. and under a pressure of 3.5 MPa, and it is coupled with a regenerator that operates at 550° C. under atmospheric pressure. The catalyst is drawn off at regular intervals at the bottom of the reactor and transferred to the regenerator, from where it is sent to the top of the reactor, whereby the transfers are made through buffer locks. At the outlet of the reactor, the unconverted ethylene is fractionated in a first distillation column and recycled. A second distillation column separates the propylene and the unconverted $C_4$ hydrocarbons that are also recycled. The composition of the metathesis effluent is indicated in Table 1, flow 8.

The overall balance of the transformation is therefore found to be as follows. Per 100 parts by weight (pp) of the $C_4$ fraction that has left the steam-cracking device, 1.6 pp of hydrogen and 28 pp of ethylene are consumed, and 27 pp of high-purity isobutene and 83 pp of "polymerization"-quality propylene are produced.

EXAMPLE 2

The first two stages of Example 1 are repeated.

In the third stage, the bottom distillation fraction that contains primarily butene-2 (composition: flow 6 of Table 2) is reacted with ethylene (overall composition: flows 6 and 7 of Table 2) on a metathesis catalyst that consists of rhenium oxide on gamma-alumina (8% by weight of metal rhenium), prepared according to the teachings of U.S. Pat. No. 4,795,734. The $C_4$ fraction is mixed at the inlet of the metathesis reactor with make-up ethylene, as well as with ethylene and butene recycling flows. This reactor operates in a moving bed, as described in Patent FR-B-2 608 595, at a temperature of 35° C. and under a pressure of 3.5 MPa, and it is coupled with a regenerator that operates at 550° C. under atmospheric pressure. The catalyst is drawn off at regular intervals at the bottom of the reactor and transferred to the regenerator, from where it is sent to the top of the reactor, whereby the transfers are made through buffer locks. At the outlet of the reactor, the unconverted ethylene is fractionated in a first distillation column and recycled. A second distillation column separates the propylene and the unconverted $C_4$ hydrocarbons that are also recycled. The composition of the metathesis effluent is indicated in Table 2, flow 8.

The overall balance of the transformation is found to be as follows. Per 100 parts by weight (pp) of the $C_4$ fraction that has left the steam-cracking device, 1.6 pp of hydrogen and 29.5 pp of ethylene are consumed, and 27 pp of high-purity isobutene and 88.5 pp of "polymerization"-quality propylene are produced.

TABLE 1

| N° de flux (FIG. 1) Composition (kg/h) | 1 Charge C4 | 1 + 2 Charge Hydro-Isomérisation | 3 Sortie Hydro-Isomérisation | 4 C4 Sortie Stabilisation | 5 Tête colonne catalytique Isobutène | 6 Pied colonne catalytique Isobutène | 6 + 7 Entrée Métathèse | 8 Sortie Métathèse |
|---|---|---|---|---|---|---|---|---|
| (C3 + C3 =) | 10 | 10 | 41 | | | | | |
| MAPD | 31 | 31 | | | | | | |
| Isobutane | 446 | 446 | 449 | 434 | 434 | | | |
| n-Butane | 545 | 545 | 988 | 981 | | 981 | 981 | 981 |
| Isobutène | 5741 | 5741 | 5738 | 5667 | 5575 | 92 | 92 | 57 |
| Butène-1 | 3407 | 3407 | 1003 | 951 | | 40 | 40 | 30 |
| Butènes-2 | 2250 | 2250 | 12737 | 12686 | | 12777 | 12777 | 1270 |
| Butadiène-1,3 | 8095 | 8095 | | | | | | |
| BBV | 104 | 104 | | | | | | |
| Hydrogène | | 343 | 16 | | | | | |
| Méthane | | 197 | 197 | | | | | |
| Ethylène | | | | | | | 5753 | 58 |
| Propylène | | | | | | | | 17162 |
| Pentènes + | | | | | | | | 85 |
| Total | 20629 | 21169 | 21169 | 20719 | 6009 | 13890 | 19643 | 19643 |

[Key to TABLE 1:]
N° de flux = Flow No.
Charge $C_4$ = $C_4$ feedstock
Charge Hydro-Isomérisation = Hydroisomerization feedstock
Sortie Hydro-Isomérisation = Hydroisomerisation outlet
C4 Sortie Stabilisation = C4 Stabilization outlet
Tête colonne catalytique Isobutène = Isobutene catalytic column head
Pied colonne catalytique Isobutène = Bottom of the isobutene catalytic column
Entrée Métathèse = Metathesis inlet
Sortie Métateèse = Metathesis outlet

TABLE 2

| N° de flux (FIG. 1) Composition (kg/h) | 1 Charge C4 | 1 + 2 Charge Hydro-Isomérisation | 3 Sortie Hydro-Isomérisation | 4 C4 Sortie Stabilisation | 5 Tête colonne catalytique Isobutène | 6 Pied colonne catalytique Isobutène | 6 + 7 Entrée Métathèse | 8 Sortie Métathèse |
|---|---|---|---|---|---|---|---|---|
| (C3 + C3 =) | 10 | 10 | 41 | | | | | |
| MAPD | 31 | 31 | | | | | | |
| Isobutane | 446 | 446 | 449 | 434 | 434 | | | |
| n-Butane | 545 | 545 | 988 | 981 | | 981 | 981 | 981 |
| Isobutène | 5741 | 5741 | 5738 | 5667 | 5575 | 92 | 92 | 57 |
| Butène-1 | 3407 | 3407 | 1003 | 951 | | 40 | 40 | 30 |
| Butènes-2 | 2250 | 2250 | 12737 | 12686 | | 13597 | 13597 | 1351 |
| Butadiène-1,3 | 8095 | 8095 | | | | | | |
| BBV | 104 | 104 | | | | | | |
| Hydrogène | | 343 | 16 | | | | | |
| Méthane | | 197 | 197 | | | | | |
| Ethylène | | | | | | | 6122 | 62 |

TABLE 2-continued

| N° de flux (FIG. 1) Composition (kg/h) | 1 Charge C4 | 1 + 2 Charge Hydro-Isomérisation | 3 Sortie Hydro-Isomérisation | 4 C4 Sortie Stabilisation | 5 Tête colonne catalytique Isobutène | 6 Pied colonne catalytique Isobutène | 6 + 7 Entrée Métathèse | 8 Sortie Métathèse |
|---|---|---|---|---|---|---|---|---|
| Propylène | | | | | | | | 18263 |
| Pentènes + | | | | | | | | 88 |
| Total | 20629 | 21169 | 21169 | 20719 | 6009 | 14710 | 20832 | 20832 |

[Key to TABLE 2:]
N° de flux = Flow No.
Charge $C_4$ = $C_4$ feedstock
Charge Hydro-Isomérisation = Hydroisomerization feedstock
Sortie Hydro-Isomérisation = Hydroisomerisation outlet
C4 Sortie Stabilisation = C4 Stabilization outlet
Tête colonne catalytique Isobutène = Isobutene catalytic column head
Pied colonne catalytique Isobutène = Bottom of the isobutene catalytic column
Entrée Métathèse = Metathesis inlet
Sortie Métateèse = Metathesis outlet The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 99/16.507, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for converting an olefinic $C_4$ fraction into high-purity isobutene and into propylene, where said fraction contains diolefins, butene-1, butenes-2, isobutene and acetylenic impurities, and where said process comprises the following successive stages:
   (1) subjecting the olefinic $C_4$ fraction to selective hydrogenation, in the presence of a catalyst, to selectively hydrogenate diolefins and acetylenic impurities and isomerize butene-1 into butenes-2, to obtain a hydrogenation effluent that contains n-butenes in a ratio corresponding to thermodynamic equilibrium, and isobutene, and that contains virtually no diolefins or acetylenic compounds;
   (2) separating by distillation the effluent from stage (1) into a top fraction that contains isobutene and a bottom fraction that contains essentially butenes-2 and butane;
   (3) subjecting the bottom fraction from stage (2) to metathesis with ethylene, in the presence of a catalyst, to obtain a metathesis effluent containing propylene; and
   (4) separating propylene from the metathesis effluent; wherein stage (2) is conducted in a distillation column that integrates hydroisomerization of butene-1, not already isomerized in stage (1), to butenes-2 and which provides a top fraction of substantially pure isobutene.

2. A process according to claim 1, wherein stage (1) is carried out by running said olefinic $C_4$ fraction in the liquid phase over a catalyst that comprises at least one metal that is selected from the group consisting of nickel, palladium and platinum, deposited on a substrate, at a temperature of 20 to 200° C., a pressure of 0.1 to 5 MPa, a volumetric flow rate of 0.5 to 10 $h^{-1}$, and with an $H_2$/diolefin molar ratio of 0.5 to 5.

3. A process according to claim 1, wherein the catalyst in stage (1) contains 0.05 to 10% by weight of sulfur.

4. A process according to claim 2, wherein the catalyst in stage (1) contains 0.05 to 10% by weight of sulfur.

5. A process according to claim 1, further comprising treating the catalyst of stage (1), before the selective hydrogenation, by at least one sulfur-containing compound that is diluted in a solvent such that the resulting catalyst contains 0.05 to 10% by weight of sulfur and activating the catalyst, loaded into a reactor for the selective hydrogenation, under a neutral atmosphere or a reducing atmosphere at a temperature of 20 to 300° C., a pressure of 0.1 to 5 MPa and a VVH of 50 to 600 $h^{-1}$.

6. A process according to claim 2, wherein the catalyst of stage (1) has been treated, before the selective by hydrogenation, by at least one sulfur-containing compound that is diluted in a solvent such that the resulting catalyst contains 0.05 to 10% by weight of sulfur and wherein the catalyst is loaded into a reactor for the selective hydrogenation and activated under a neutral atmosphere or a reducing atmosphere at a temperature of 20 to 300° C., a pressure of 0.1 to 5 MPa and a VVH of 50 to 600 $h^{-1}$.

7. A process according to claim 1, wherein the catalyst of stage (1) consists essentially of palladium that is deposited on alumina, and sulfur.

8. A process according to claim 2, wherein the catalyst of stage (1) consists essentially of palladium that is deposited on alumina, and sulfur.

9. A process according to claim 6, wherein the column that integrates the isomerization of butene-1 to butenes-2 comprises, on the inside or outside, one or more feedstocks of a catalyst as defined for use in stage (1).

10. A process according to claim 1, wherein the metathesis is carried out in stage (3) in the presence of a catalyst that comprises at least one rhenium oxide that is deposited on a substrate, at a temperature of 0 to 100° C. and at a pressure that is at least equal to the vapor pressure of the reaction mixture at the reaction temperature.

11. A process according to claim 10, wherein the stage (3) catalyst contains 0.01 to 20% by weight rhenium oxide, expressed in metallic rhenium, deposited on a substrate that contains at least 75% by weight of alumina and 0.01 to 30% by weight of at least one oxide of niobium or tantalum.

12. A process according to claim 1, wherein the metathesis is carried out with a moving-bed catalyst.

13. A process according to claim 10, wherein the metathesis is carried out with a moving-bed catalyst.

14. A process according to claim 1, wherein the olefinic $C_4$ fraction is a steam-cracking fraction.

15. A process according to claim 14, wherein the ethylene that is used in the metathesis stage (3) is obtained from a steam-cracking operation.

16. A process according to claim 1, wherein the bottom fraction of stage (2) contains at most 1% by weight of isobutene and at most 1% by weight of butene-1.

17. A process according to claim 1, wherein the integrated hydroisomerization of butene-1 in stage (2) is conducted in the presence of a catalyst that contains 0.05 to 10% by weight of sulfur.

18. A process according to claim 1, wherein the integrated hydroisomerization of butene-1 in stage (2) is conducted in the presence of a catalyst that is treated by at least one sulfur-containing compound that is diluted in a solvent such that the resulting catalyst contains 0.05 to 10% by weight of sulfur and activating the catalyst, loaded into a reactor for the selective hydrogenation, under a neutral atmosphere or a reducing atmosphere at a temperature of 20 to 300° C., a pressure of 0.1 to 5 MPa and a VVH of 50 to 600 $h^{-1}$.

19. A process according to claim 1, wherein the integrated hydroisomerization of butene-1 in stage (2) is conducted in the presence of a catalyst that consists essentially of palladium that is deposited on alumina, and sulfur.

20. A process according to claim 1, further comprising passing the effluent from stage (1), before stage (2), through a stablization column that eliminates traces of gaseous hydrocarbons that may be present in the hydrogen used for the hydrogenation.

* * * * *

UNITED STATES PATENT AND TRADEMARK OFFICE
CERTIFICATE OF CORRECTION

PATENT NO. : 6,686,510 B2
DATED : February 3, 2004
INVENTOR(S) : Dominique Commereuc et al.

It is certified that error appears in the above-identified patent and that said Letters Patent is hereby corrected as shown below:

Column 10,
Line 39, reads "selective by" should read -- selective --

Column 12,
Line 14, reads "a stablization column" should read -- a stabilization column --

Signed and Sealed this

Twenty-eighth Day of December, 2004

JON W. DUDAS
*Director of the United States Patent and Trademark Office*